United States Patent [19]
Stine et al.

[11] Patent Number: 5,856,604
[45] Date of Patent: Jan. 5, 1999

[54] PROCESS FOR INTEGRATED OLIGOMER PRODUCTION AND SATURATION

[75] Inventors: Laurence O. Stine, Western Springs; Steven C. Gimre, Carol Stream, both of Ill.

[73] Assignee: UOP LLC, Des Plaines, Ill.

[21] Appl. No.: 936,942

[22] Filed: Sep. 23, 1997

[51] Int. Cl.[6] .................................................. C07C 2/00
[52] U.S. Cl. ........................ 585/310; 585/255; 585/330
[58] Field of Search ..................................... 585/255, 310, 585/330; 208/62, 64, 65

[56] References Cited

U.S. PATENT DOCUMENTS

| | | | |
|---|---|---|---|
| 2,526,966 | 10/1950 | Oberfell et al. | 196/1 |
| 3,745,112 | 7/1973 | Rausch | 208/139 |
| 4,304,948 | 12/1981 | Vora et al. | 585/315 |
| 4,393,259 | 7/1983 | Ward et al. | 585/315 |
| 4,542,247 | 9/1985 | Chang et al. | 585/330 |
| 4,678,645 | 7/1987 | Chang et al. | 422/190 |
| 4,749,820 | 6/1988 | Kuo et al. | 585/330 |
| 4,788,364 | 11/1988 | Harandi | 585/330 |
| 5,049,360 | 9/1991 | Harandi et al. | 422/141 |
| 5,498,811 | 3/1996 | Perego et al. | 585/330 |

FOREIGN PATENT DOCUMENTS 2186287  8/1987  United Kingdom .

*Primary Examiner*—Walter G. Griffin
*Attorney, Agent, or Firm*—Thomas K. McBride; John G. Tolomei

[57] ABSTRACT

A process for the production motor fuel components from isoparaffins by dehydrogenation, oligomerization and saturation uses a single compressor to provide all feed and recycle requirements within the process arrangement. The single compressor can be employed for the integration of all three processes while surprisingly reducing equipment requirements throughout the integrated process arrangement. The compressor raises the effluent pressure of the effluent from the dehydrogenation zone to a level that eliminates the need for any additional compression for the recycle of hydrogen to the saturation zone, eliminates the need for refrigeration to recover butanes from the dehydrogenation zone effluent and allow an essentially complete elimination of heavies from the feed to the oligomerization reaction zone.

17 Claims, 2 Drawing Sheets

PROCESS FOR INTEGRATED OLIGOMER PRODUCTION AND SATURATION

FIELD OF THE INVENTION

This invention relates generally to the production of gasoline boiling range hydrocarbons by the dehydrogenation of light paraffins, the oligomerization of light olefins and the hydrogenation of the resulting oligomers.

BACKGROUND OF THE INVENTION

Prior Art

A continuing demand exists for the conversion of isobutane and light olefins into high octane motor fuels. The alkylation of isobutane with propylene, butenes and amylenes using a hydrofluoric acid (HF) catalyst, commonly referred to as HF alkylation, has provided a highly successful method for the production of high octane motor fuels. Despite a long history of safe operation, recent concerns over the possibility of a catastrophic release of HF acid from HF alkylation units has prompted the investigation of modifications or alternatives to the HF alkylation process for the production of motor fuels. One existing alternative is a similar alkylation process that uses sulfuric acid as the catalyst. While the use of sulfuric acid may decrease the degree of the hazard that some associate with the use of HF acid, sulfuric acid processes are still perceived as possibly presenting the same hazard and are not as economically advantageous as the HF alkylation process. Therefore, processing substitutes for the HF alkylation process are still sought.

Other methods of combining isobutane with light olefins to produce motor fuels are known and practiced; however, they do not produce the same quality gasoline products or are more expensive to install and operate. One such alternative is the dehydrogenation of butanes and the oligomerization of the resulting olefins to produce gasoline boiling range hydrocarbons. The oligomerization of light olefins into higher molecular weight motor fuels using a solid phosphoric acid is well known and its use predates the HF alkylation process. Such oligomerization processes are also referred to as catalytic condensation and polymerization with the resulting motor fuel often referred to as polymer gasoline. Patents disclosing the combination of dehydrogenation of light paraffin streams with oligomerization of the resulting dehydrogenation effluent include U.S. Pat. Nos. 4,393,259; 5,049,360; 4,749,820; 4,304,948 and 2,526,966.

It also known to hydrotreat the olefinic hydrocarbon streams produced by oligomerization to saturate olefins. Patent GB 2186287 discloses dehydrogenation of and oligomerization of a $C_4$ fraction to produce a jet aircraft fuel that is optionally hydrogenated. The hydrotreatment of jet fuels, diesel fuels and lubes produced by dehydrogenation and oligomerization of light paraffins is disclosed in U.S. Pat. No. 4,678,645. However, hydrotreating is not always beneficial for gasoline fractions produced by oligomerization and can lower octane ratings, but is known to be particularly beneficial when saturating isooctenes to isooctane gasoline.

An arrangement for producing alkylate quality feedstocks by the combination of dehydrogenation, oligomerization and saturation is disclosed in copending U.S. Ser. No. 08/573,089.

It is an object of this invention to provide an alternative to HF alkylation for the combination of isobutane with light olefins that advantageously produces a comparable motor fuel product in an integrated series of dehydrogenation, oligomerization and saturation steps in a more cost effective manner using a reduced amount of equipment.

BRIEF SUMMARY OF THE INVENTION

This invention integrates the dehydrogenation of an isobutane-containing stream with the oligomerization of the resulting isobutenes and saturation of the resulting oligomers in a manner that uses a single compressor to effect all gas circulation through the process and improve the efficiency of stream separations. The process thereby produces a motor fuel equivalent to that produced by HF alkylation in a more efficient manner than has been previously attained in prior integrations.

The single compressor location receives the effluent from the dehydrogenation zone and raises the pressure from typically low effluent pressure of less than 100 psig to more than 450 psig and typically to about 550 psig. Generally the only treatment of the dehydrogenation zone effluent before compression is cooling to reduce the temperature. Pressurizing the effluent of the dehydrogenation zone to 450 psig, or higher, provides enough pressure head to circulate all gas streams through the remaining process zones. Moreover, providing all the compression at a single location raises the pressure at the dehydrogenation separation stages to the point of providing an essentially complete elimination of heavy ends from the dehydrogenation zone effluent, which allows a recovery of high purity hydrogen without refrigeration. Therefore, aside from the elimination of additional compression equipment, the single location compression has additional separation and recovery benefits as well.

The process can be operated with high conversion or low conversion dehydrogenation zones. High conversion dehydrogenation zones will typically have a single feed to the process with the dehydrogenation zone providing all of the necessary olefins for the oligomerization feed and all of the required hydrogen for the saturation of oligomers. The high conversion dehydrogenation zone typically operates at lower pressure and will, therefore, push the compressor of this invention to operate with a higher compression ratio. The low conversion dehydrogenation zone reduces operational costs and complements the operation of the oligomerization zone by providing unreacted feed components that serve as a diluent. Higher pressures associated with the operation of the low conversion dehydrogenation zone also reduce the compression ratio at the single compressor location. However, lower conversion may require the addition of supplemental olefins to provide the desired olefin concentration in the oligomerization zone feed and additional hydrogen for the saturation zone.

In a preferred form, the invention uses a deisobutanizer column as a primary fractionator to supply feed to a low conversion dehydrogenation zone and to recover motor fuel product components. In this preferred form of the invention, the isobutane-containing input stream enters the process via the primary fractionator that provides a sidecut to supply the isobutane feed stream to the dehydrogenation zone.

In application of the process to larger units that have a large amount of isobutane recycle, it may be desirable to use separate columns for the feed and recycle butanes. The feed may be advantageously fractionated in a separate deisobutanizer column for the recovery of relatively high purity isobutane. Unconverted isobutane from the oligomerization zone may be recovered in a separate debutanizer column and passed directly to the dehydrogenation zone. The use of separate deisobutanizer will result in a smaller column. A portion of the debutanizer overhead may be passed to the deisobutanizer to increase the overall purity of isobutane that is recycled to the dehydrogenation zone.

Accordingly, in a broad embodiment, this invention is a process for the production of a motor fuel product from an isobutane-containing input stream. The process passes at least a portion of the input stream comprising isobutane to a dehydrogenation zone and contacts $C_4$ hydrocarbons in the dehydrogenation zone with a dehydrogenation catalyst at dehydrogenation conditions including a temperature of 950° to 1200° F., a pressure of from 5 to 150 psig, and an LHSV of 0.5–50. The process recovers a dehydrogenation effluent comprising $C_4$ isoolefins, isobutane, and hydrogen. At least a portion of the dehydrogenation zone effluent passes to a single compressor location in the process arrangement. The compressor compresses the effluent to a pressure of at least 450 psig to produce a compressed effluent. The compressed effluent enters a first separator and the separator recovers a first separator stream comprising hydrogen at a pressure of from 400 to 600 psig and a dehydrogenated fraction comprising $C_4$ olefins and paraffins in a liquid phase. At least a portion of the dehydrogenated fraction passes to an oligomerization zone as an oligomerization feed. The process contacts the oligomerization zone feed with a solid oligomerization catalyst at oligomerization conditions including a temperature of 200° to 500° F., a pressure of 400 to 600 psig, and an LHSV of 0.8 to 5 to produce an oligomerization effluent comprising $C_7$ and higher isoolefins. At least a portion of the effluent from the oligomerization zone passes into a saturation zone with at least a portion of the first separator stream passing directly into the saturation zone or into combination with the portion of the oligomerization zone effluent directed to the saturation zone. The saturation zone contacts the oligomerization zone effluent and hydrogen with a saturation catalyst at saturation conditions to saturate olefins in the oligomerization effluent and produces a saturation zone effluent stream for recovery. At least a portion of the saturation zone effluent stream passes to a second separator that recovers a second separator stream comprising $C_7$ or higher hydrocarbons in liquid phase and a third separator stream comprising $C_4$ and lower boiling hydrocarbon vapors. The process passes a first portion of the second separator stream to the oligomerization zone as a recycle stream and recovers the motor fuel product from a second portion of the second separator stream.

Other objects, embodiments and details of this invention will be provided in the following detailed disclosure of the invention.

BRIEF DESCRIPTION OF THE DRAWINGS

The FIGURE contained on two sheets as FIG. 1A and FIG. 1B respectively is a schematic process flow diagram of the invention showing principal processing zones, the single compressor location, and heat exchange and processing steps.

DETAILED DESCRIPTION OF THE INVENTION

Figure 1A:
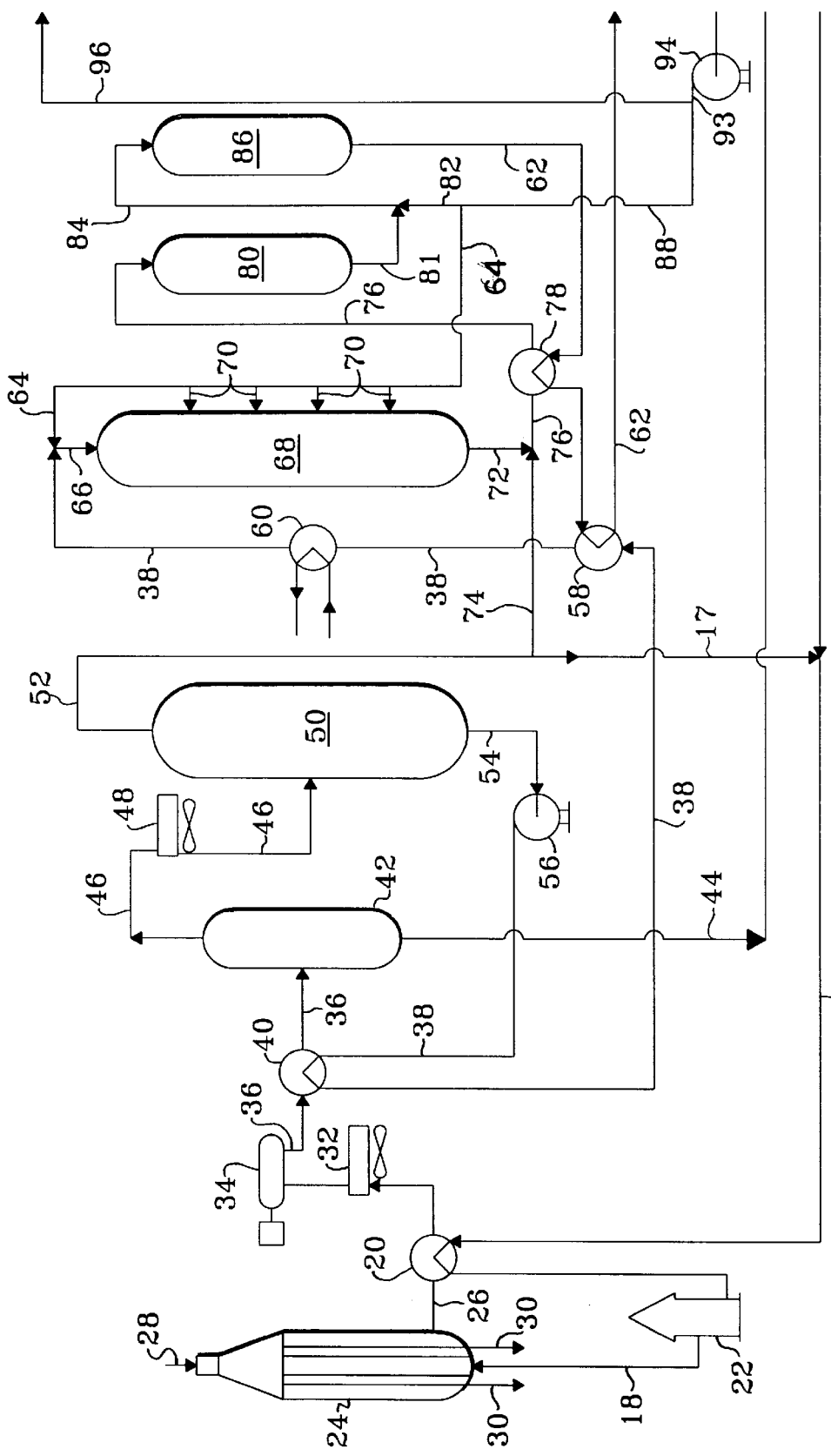
Figure 1B:
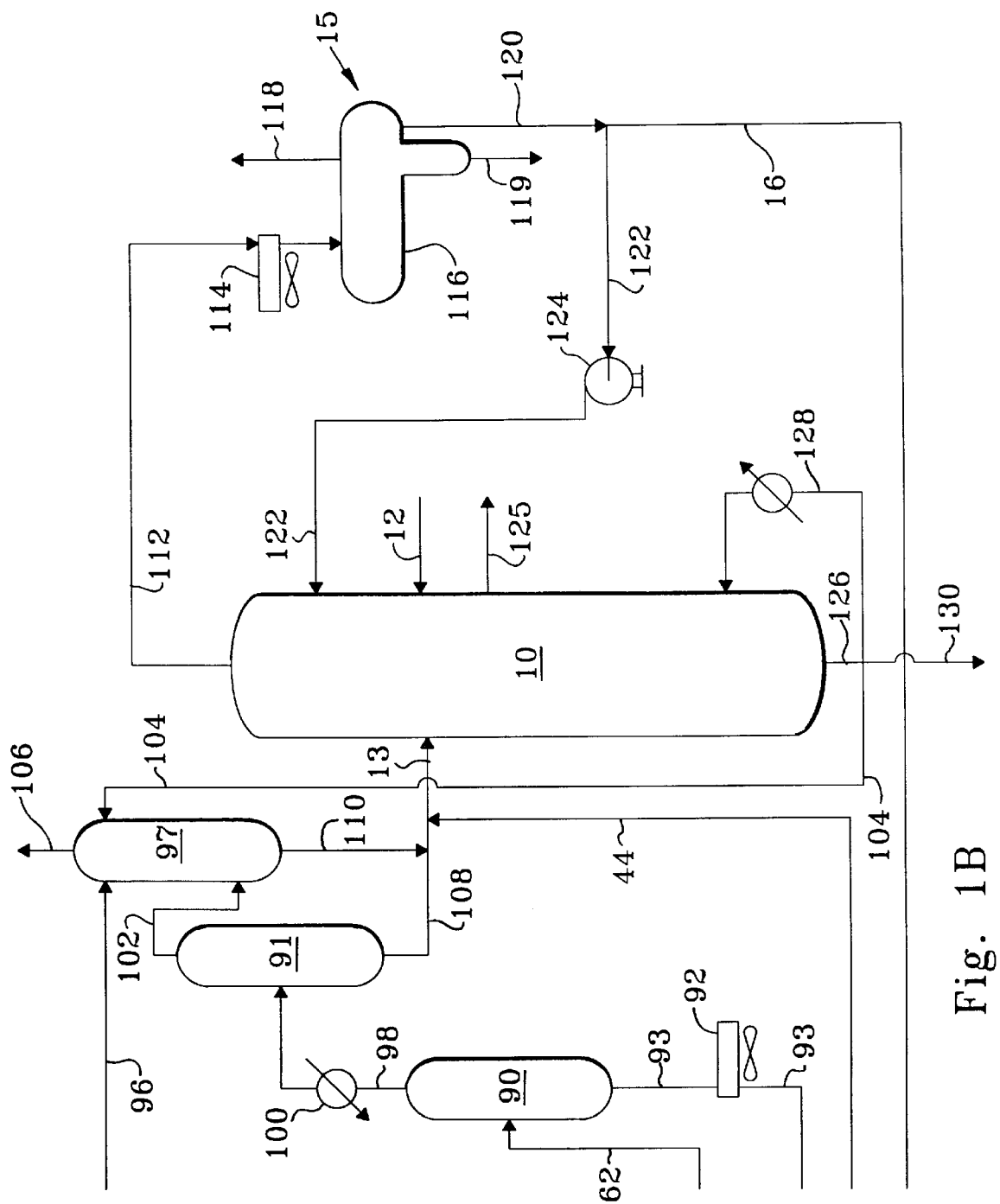

The process and different operational steps will be described in conjunction with the FIGURE. The FIGURE shows only one form of the invention and only those portions of the process that are necessary to gain an understanding of the invention and the necessary means of integrating the different process steps that comprise the invention. Further details related to valves, control means, heaters, coolers, and other necessary processing equipment are well known to those skilled in the art and are not described in detail unless necessary for an understanding of the invention.

The primary feed to the process unit enters a deisobutanizer column 10 via a line 12. Direct entry of the feed into a deisobutanizer column is believed to offer the most advantageous location for the input of the primary feed, but the primary feed may enter the process at other locations. One alternate location for the primary feed would include direct entry into the dehydrogenation zone.

Line 12 typically delivers the primary feed stream to an intermediate tray level of column 10. Column 10 also receives recycle material from a hereinafter described saturation zone effluent stream via a line 13. Deisobutanizer column 10 includes an overhead section 15 that delivers a net overhead stream 16 comprising the feed stream isobutane. A line 17 admixes a hydrogen-containing stream with stream 16 to provide a combined feed in a line 18. Line 18 passes the dehydrogenation zone feed through exchanger 20 to recover heat from the dehydrogenation zone effluent. Heating continues as line 18 passes the combined feed through heater 22. Depending on the composition of the dehydrogenation catalyst, a small amount of sulfur may be added upstream of the heaters and reactors to prevent carbon formation on metallic surfaces of the reactors and heaters and to passivate the catalyst. Line 18 passes the heated feed into a dehydrogenation reactor 24. Contact with a dehydrogenation catalyst dehydrogenates a portion of the paraffin components from the feed stream which pass out of dehydrogenation zone reactor 24 via a line 26. The dehydrogenation zone reactor is shown in simplified form and will usually include at least two separate reactor vessels with an interheater staged ahead of each additional reactor stage to provide heat for the endothermic reaction.

The FIGURE also shows schematically the operation of the dehydrogenation zone with a continuous catalyst replacement via a catalyst transfer line 28 and catalyst withdrawal lines 30. A catalyst regeneration system (not shown) supplies regenerated catalyst to line 28 and recovers catalyst from lines 30 via a catalyst transfer system (not shown). The catalyst regeneration section reconditions catalyst by well known methods of coke combustion and metals treatment.

The effluent from the dehydrogenation reaction zone contains at least hydrogen, butane, butenes, some light hydrocarbons and small amounts of heavy hydrocarbons comprising mainly xylenes and aromatics. Line 26 passes the effluent from the dehydrogenation reaction zone through exchanger 20, a cooler 32 and into the inlet of a compressor 34. Compressor 34 compresses the effluent from the dehydrogenation zone to a sufficient pressure to supply all of the gas phase transport throughout the process arrangement. The compressor discharge exits through a line 36 and is cooled against a separator bottoms stream carried by a line 38 in an exchanger 40. Line 36 discharges the compressed dehydrogenation effluent into a heavies separator 42. Heavies separator 42 removes the various heavy hydrocarbon components from the compressed effluent stream via line 44. A line 46 carries the vapor effluent from heavies separator 42 through a cooler 48 and into a hydrogen separator 50 for the recovery of a hydrogen-containing stream via a line 52. Line 52 recycles hydrogen to the dehydrogenation zone feed via line 17. The dehydrogenation zone of this invention operates with a relatively pure hydrogen stream that is readily supplied with by the simple arrangement of separator 50. The high pressure resulting from the single compressor location will normally give stream 52 a hydrogen concentration of 80 mol wt % or more without chillers or more intensive separation arrangements. The remaining components of the hydrogen-containing stream comprises $C_1$–$C_3$ hydrocarbons and typically additional smaller concentrations of $C_4$ hydrocarbons. The remainder of the hydrogen-containing stream recovered from separator 50 serves as a hydrogen feed to the saturation reactor as hereinafter described.

A bottoms stream 54 from separator 50 provides at least a portion of the feed to the oligomerization zone. The separator bottoms stream may be combined with a secondary feed stream containing olefins to form a combined feed to the oligomerization zone. A pump 56 passes the separators bottoms stream via line 38 through exchanger 40, exchanger 58 and heater 60. Exchanger 58 recovers heat from a saturation effluent stream carried by a line 62. Line 38 optionally combines the heated stream with a hereinafter described recycle stream 64 which typically comprises $C_8$ and heavier paraffins. A line 66 charges the oligomerization feed to an oligomerization reactor 68. The olefins entering through line 66 will include normal butenes and isobutene and may also include $C_3$ and $C_5$ olefins as well some paraffins.

Although only one reactor is depicted, the oligomerization zone typically contains a plurality of parallel oligomerization reactors and the oligomerization feed is typically divided to pass through a series of oligomerization reactors. Reactor 68 is divided into multiple stages. A distribution system supplies quench to each stage from line 64 via quench distribution lines 70. Effluent piping 72, connected to the outlet of the oligomerization reactor 68, recovers an oligomerization effluent stream.

A line 74 supplies hydrogen from line 52 to the effluent 72 to produce a combined feed for the saturation reaction zone. Line 76 receives the combined feed for the saturation process which is heated in exchanger 78 against the saturation effluent 62. When the hydrogen from the dehydrogenation process is insufficient to supply the saturation requirements, particularly in low dehydrogenation conversion cases, then outside make-up hydrogen may be charged to the process. The preferred location for the addition of make-up hydrogen is upstream of compressor 34 where plant hydrogen is likely to have sufficient pressure to enter the system. Preferably all of the effluent from the oligomerization zone passes, together with the added hydrogen, directly into a saturation zone.

The saturation zone saturates the unsaturated gasoline boiling range components from the oligomerization zone to provide a product stream having alkylate quality gasoline components. The saturation zone will typically use a plurality of reactors 80, 86 arranged in series with feed passing through each reactor. The series reactor arrangement permits greater control of temperatures.

Line 76 carries the combined feed 62 into a first saturation reactor 80. The preferred arrangement of the hydrogenation zone will be a two stage hydrotreating reactor system wherein the effluent from the first saturation reactor 80 passes via lines 81 and 84 into a second reaction zone 86. To control the temperature exotherm from the first reaction zone, a portion of a recycle stream from a line 88 may pass via a line 82 into combination with the first reaction zone effluent 81. The now saturated oligomerization reaction zone effluent passes via line 62 from reactor 86 through heat exchangers 78 and 58 to transfer heat before entering a hot separator 90.

Hot separator 90 together with a cold separator 92 and adsorber 94 disclose one possible arrangement for recovering recycle hydrocarbons, discharging light ends and transferring product hydrocarbons to primary separator 10. Recycle materials consisting mainly of $C_{12}$ and heavier saturated hydrocarbons exit the bottom hot separator 90 via line 88. Hot separator 90 recovers saturated heavy material from the saturation zone to provide a liquid stream 93 for intermediate quench in the saturation zone and flushing of heavy hydrocarbons from the surface of the oligomerization catalyst. After cooling in cooler 92, pump 94 discharges the saturated hydrocarbons from line 93 for division into two streams. A line 96 withdraws a portion of the saturated hydrocarbons while the remainder of the recycle material passes to the saturation and oligomerization reactors via line 88 as previously described. Lighter hydrocarbons pass overhead from hot separator 90 via a line 98 and pass through a cooler 100 before entering cold separator 91. An overhead stream consisting mainly of hydrogen and $C_1$–$C_3$ hydrocarbons with lesser amounts of $C_4$ hydrocarbons passes overhead from cold separator 91 via a line 102 into an absorber vessel 97. The heavy saturated hydrocarbons taken by line 96 from the bottoms of hot separator 90 or a portion of the product stream taken from the bottom of primary separation vessel 10 via a line 104 can serve as the absorbent in vessel 97 to recover additional amounts of $C_4$ hydrocarbons. The remaining $C_3$ and lighter materials pass overhead from absorber vessel 97 via line 106. Cold separator bottoms comprising the $C_4$ and heavier hydrocarbons pass from cold separator 91 via a line 108 in admixture with $C_4$ hydrocarbons carried by an absorbent stream 110 that exits the bottom of absorber vessel 97. Additional heavy hydrocarbons removed from the dehydrogenation zone effluent and carried by line 44 combine with the saturated streams from cold separator 91 and adsorber 97 to provide the product input stream which enters primary separator 10 via line 13. Feed hydrocarbons for the dehydrogenation zone, along with lighter hydrocarbons, pass overhead from adsorber vessel 10 via a line 112 through a cooler 114 and into an overhead receiver 116. An off gas stream comprising mainly non-condensible hydrocarbons passes out of the overhead receiver 116 via line 118. An aqueous phase flows out of receiver 116 via a line 119. Liquid phase hydrocarbons pass from receiver 116 via a line 120 which supplies feed hydrocarbons to line 16 and a reflux stream 122. A pump 124 returns reflux to the adsorber vessel 10 via line 122. Primary separator 10 may also supply a sidecut stream 125 of normal butane for isomerization and return to the primary separator.

Line 126 withdraws a product stream comprising alkylate quality $C_8$ saturated hydrocarbons and heavier hydrocarbons. Line 126 supplies a reboiler stream 128 and optional reflux stream 104. The net product exits the process through a line 130.

The primary feed will typically comprise a refinery paraffin stream that contains at least 20 wt % isobutane. Preferred feeds are rich in $C_4$ paraffins and contain a high percentage of isobutane. (The term "rich," when used herein, means a stream having a weight or volume percent content of at least 50% of the mentioned component while the term "relatively rich" means a stream having a higher concentration of the mentioned component than the feed from which it was derived.) Preferred feeds for this process are rich in isobutane and will more preferably have an isobutane concentration in a range of from 55 to 99 wt %. Typical sources for this feed stream are field butanes, refinery $C_4$ saturate streams, effluents from butane isomerization, and butanes from gas recovery units. The isobutane stream can be obtained from refinery butane streams or other sources that will provide a butane rich feed.

The preferred main separator arrangement of this process facilitates the use of relatively impure isobutane-containing streams. To a substantial degree, the primary separator can prefractionate higher and lower boiling hydrocarbons from the feed for the dehydrogenation zone. Thus, feeds containing isobutane with substantial quantities of other hydrocarbons can still provide acceptable feed sources.

The preferred deisobutanizer arrangement performs a simultaneous distillation of the product containing separator streams along with the initial refinery $C_4$ input stream. The process can also arrange the primary separator as deisobutanizer vessel separates that separates off the light ends as an overhead stream while simultaneously supplying the previously described dehydrogenation zone input stream as a sidecut.

The preferred arrangement of the primary separator is as a single deisobutanizer column. Integration of the deisobutanizer column into simultaneous feed and product separation allows the process to efficiently perform the necessary distillations for the successful operation of the process. Integration of multiple feed inputs and stream outputs on the deisobutanizer column promotes separation efficiency by permitting matching of stream compositions with column locations in a manner that reduces the overall size of the deisobutanizer column. The deisobutanizer column design is arranged to provide the high concentration of the isobutanes in the feed to the dehydrogenation zone via either an overhead or a sidecut stream. The deisobutanizer will typically provide an isobutane purity of 80 wt % and more preferably at least 95 wt %. The column also operates to separate remaining $C_4$ minus materials from the dehydrogenation zone feed stream via an off-gas stream. The carry over of $C_3$ hydrocarbons with the dehydrogenation zone feed stream does not present a problem for the column operation. Propane carried over with the feed from the column undergoes dehydrogenation in the dehydrogenation zone with a subsequent increase in oligomerization product.

As described in connection with the drawings, the isobutane-containing feed will often contain large proportions of normal butane. The primary fractionator will normally provide an additional sidecut stream for the recovery of a normal butane-containing stream. It may often be desirable to send this stream to a butane isomerization zone to obtain additional isobutane for input to the process.

The isobutane rich sidecut stream from the deisobutanizer passes to the dehydrogenation reaction zone. Suitable dehydrogenation reaction zones for this invention beneficially integrate the dehydrogenation zone with the oligomerization reaction zone and can operate at high or low conversion conditions. Lower conversion conditions and the typically accompanying higher pressure will reduce catalyst deactivation and allow most dehydrogenation reaction zones to operate with reduced regeneration requirements. In addition, higher pressure conditions reduce compression ratio requirements for effluent separation and improve process efficiency. The lower severity dehydrogenation zone reaction conditions also provide an unreacted mass flow of butane which facilitates the temperature control necessary for the condensation reactions. The reduced quantity of olefins produced by lower conversion conditions may be supplemented by the addition of a secondary feed that is preferably rich in olefins.

The dehydrogenation section may use any type of reactor that will dehydrogenate the isobutane to isobutylene. Catalytic dehydrogenation is an established hydrocarbon conversion process employed in the petroleum processing industry for producing olefins from paraffinic feedstocks. The art of catalytic dehydrogenation is well known. Briefly, suitable dehydrogenation processes will admix a feedstock with a stream comprising hydrogen and will contact the feed with catalyst in a reaction zone. As previously stated, the preferred feedstocks for catalytic dehydrogenation of this invention predominately comprise isobutane and may also contain propane and pentanes. The catalytic dehydrogenation process will treat the substantially paraffinic hydrocarbons to thereby form olefinic hydrocarbon compounds.

Any suitable dehydrogenation catalyst may be used in the process of the present invention. The particular dehydrogenation reactor configuration will depend on the performance characteristics of the catalyst and the reaction zone. The olefin yield from the dehydrogenation reactor will usually be in a range of 10 to 30 wt %. Operating conditions within the dehydrogenation zone are also chosen to produce an olefin effluent stream having an isobutene to normal butene ratio of more than 1. The use of low conversion conditions within the dehydrogenation zone can extend the cycle life of the catalyst to at least 4 days and more typically 6 days. Any suitable method can regenerate the catalyst such as a swing bed or continuous catalyst regeneration procedures.

A catalytic dehydrogenation reaction is normally effected in the presence of catalyst particles comprised of one or more Group VIII nobel metals (e.g., platinum, iridium, rhodium, palladium) combined with a porous carrier, such as a refractory inorganic oxide. Generally, the preferred catalyst comprises a platinum group metal component, an alkali metal component with the porous carrier. The catalyst may also contain promoter metals which advantageously improve the performance of the catalyst. It is preferable that the porous carrier material of the dehydrogenation catalyst be an absorptive high surface area support having a surface area of about 25 to about 500 $m^2/g$. The porous carrier material should be relatively refractory to the conditions utilized in the reaction zone and may be chosen from those carrier materials which have traditionally been utilized in dual function hydrocarbon conversion catalysts. A porous carrier material may, therefore, be chosen from an activated carbon, coke or charcoal, silica or silica gel, clays and silicates including those synthetically prepared and naturally occurring, which may, or may not, be acid-treated as, for example, attapulgus clay, diatomaceous earth, kieselguhr, bauxite; refractory inorganic oxide such as alumina, titanium dioxide, zirconium dioxides, magnesia, silica alumina, alumina boria; crystalline alumina silicates such as naturally occurring or synthetically prepared mordenite or a combination of one or more of these materials or other zeolite materials. The preferred porous carrier material is a refractory inorganic oxide, with the best results being obtained with an alumina carrier material. Alumina is the most commonly used carrier. The preferred alumina materials are known as the gamma, eta and theta alumina with gamma and theta alumina giving the best results. The preferred catalyst will have a theta alumina carrier which is in the form of spherical particles. Particles having relatively small diameters on the order of about $\frac{1}{16}$" are preferred, but the particles may be as large as $\frac{1}{4}$".

Of the platinum group metals which include palladium, rhodium, ruthenium, osmium or iridium, the use of platinum is preferred. The platinum group component may exist within the final catalyst composite as a compound such as an oxide, sulfide, halide, oxysulfide, etc., of an elemental metal, or it may exist in combination with one or more other ingredients of the catalyst. It is believed that the best results are obtained when substantially all of the platinum group components exist in the elemental state. The platinum group components generally comprises from about 0.01 to about 2 wt. % of the final catalytic composite, calculated on an elemental basis. It is preferred that the platinum content of the catalyst be between about 0.2 and 1 wt %. The preferred platinum group component is platinum, with palladium being the next preferred metal. The platinum group component may be incorporated into the catalyst composite in any suitable manner such as by coprecipitation or cogelation with the preferred carrier material or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

The preferred alkali metal is normally either potassium or lithium, depending on the feed hydrocarbon. The concentration of the alkali metal may range from about 0.1 to 3.5 wt %, but is preferably between 0.2 and about 2.5 wt % calculated on an elemental basis. This component may be added to the catalyst by the methods described above as a separate step or simultaneously with the solution of another component.

As noted previously, the dehydrogenation catalyst may also contain a promoter metal. One such preferred promoter metal is tin. The tin component should constitute about 0.01 to about 1 wt % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble, decomposable compound of tin to impregnate the calcined porous carrier material. A more detailed description of the preparation of the carrier material and the addition of platinum component and the tin component to the carrier material may be obtained by reference to U.S. Pat. No. 3,745,112.

The low severity operation of the preferred dehydrogenation zones will result in an extended catalyst life. Depending on the catalyst system and the properties of the dehydrogenation zone feed, the dehydrogenation reaction zone will use a solid catalyst that can operate as a fixed bed, a semi-regenerated bed or continuous catalyst regeneration. The actual arrangement of the dehydrogenation zone may be relatively simple and include a single reactor and single heater. Moreover, the dehydrogenation catalytic reaction zone may consist of multiple catalyst beds. In one such system, the catalyst is employed within an annular bed through which it is movable via gravity flow.

During the course of a dehydrogenation reaction, catalyst particles become deactivated as a result of mechanisms such as the deposition of coke on the particles; that is, after a period of time in use, the ability of catalyst particles to promote dehydrogenation reactions decreases to the point that the catalyst is no longer useful. The catalyst must be reconditioned, or regenerated, before it can be reused in a dehydrogenation process.

In such systems, it is common practice to remove catalyst from the bottom of the reaction zone, regenerate it and then return it to the top of the reaction zone. Preferred methods of dehydrogenating light hydrocarbons suitable for the continuous dehydrogenation of isobutane using a continuous catalyst regeneration system are described in U.S. Pat. Nos. 5,227,566, 3,978,150, 3,856,662, 3,854,887, 3,839,197, 3,825,116, and 3,706,536; the contents of which are hereby incorporated by reference.

In preferred form, the dehydrogenation process will employ a moving bed reaction zone and regeneration zone. Moving bed systems advantageously maintain production while the catalyst is removed or replaced. In a typical moving bed reaction zone fresh catalyst particles are fed through the reaction zones by gravity. Catalyst is withdrawn from the bottom of the reaction zone and transported to a regeneration zone where a hereinafter described multi-step regeneration process is used to recondition the catalyst to restore its full reaction promoting ability. Catalyst flows by gravity through the various regeneration steps and then is withdrawn from the regeneration zone and furnished to the reaction zone. Movement of catalyst through the zones is often referred to as "continuous" though, in practice, it is "semi-continuous." By "semi-continuous" movement is meant the repeated transfer of relatively small amounts of catalyst at closely spaced points in time. For example, one batch per minute may be withdrawn from the bottom of a reaction zone and withdrawal may take one-half minute, that is, catalyst will flow for one-half minute. If the inventory in the reaction zone is large, the catalyst bed may be considered to be "continuously" moving.

In the preferred regeneration method for the dehydrogenation process of this invention, catalyst is contacted with a hot oxygen-containing gas stream (known as recycle gas) in order to remove coke which accumulates on surfaces of the catalyst while it is in a dehydrogenation reaction zone. Coke is comprised primarily of carbon, but it is also comprised of a relatively small quantity of hydrogen. The mechanism of coke removal is oxidation to carbon monoxide, carbon dioxide, and water. Coke content of spent catalyst may be as much as 20% of the catalyst weight, but 5–7% is a more typical amount. Within the combustion zone, coke is usually oxidized at temperatures ranging from about 850° F. (471° C.) to about 1000° F. (538° C.), but temperatures in localized regions may reach 1100° F. (593° C.) or more.

Oxygen for the combustion of coke typically enters what is called a combustion section of the regeneration zone in what has been termed a recycle gas. The recycle gas contains a low concentration of oxygen usually on the order of 0.5 to 1.5% by volume. The remainder of the recycle gas is usually composed mainly of inert combustion by-products. A system of blowers, heaters and coolers maintains circulation and the temperature of the recycle gas in a recycle loop. A small quantity of the recycle gas stream is vented and replaced with a make-up stream of air or other oxygen-containing gas to maintain the dilute oxygen concentration in the recycle gas stream. The low oxygen level is maintained for temperature control.

It is also possible to use steam as a diluent for the combustion gas stream and avoid the circulation of recycle gas. The low severity conversion conditions within the dehydrogenation zone result in a low coke load on the regeneration zone. The low coke loading requires only a small regeneration zone to provide sufficient coke combustion. Relatively small amounts of steam can be used to dilute an oxygen-containing stream to sufficiently low $O_2$ levels for a controlled heat release in the regeneration zone. Instead of air, a relatively pure oxygen stream may be preferred for admixture with the steam. The use of the preferred theta alumina catalyst will also provide the necessary resistance to hydrothermal deactivation of the catalyst for repeated regenerations with the steam diluent.

In addition to combustion the regeneration normally includes steps of drying and redispersion. The catalyst particles can pass directly from the combustion zone directly into a drying zone where the water that is left on the catalyst particles after the combustion process is removed. Water is evaporated from the surface and pores of the catalyst particles by contact with a heated gas stream. Exposure to reactants in a wet reduction zone and the exposure to high temperatures and steam in the combustion zone serve to agglomerate the platinum on the surface of the catalyst. Once the coke has been removed and the catalyst particles are in various states of oxidation, contact of the catalyst at a temperature between about 800° F. (426° C.) and 1100° F. (593° C.) in a chlorine environment will re-disperse the platinum over the surface of the catalyst support. The arrangement of a typical combustion, drying and redispersion sections may be seen in U.S. Pat. Nos. 3,653,231 and 5,227,566; the contents of which are hereby incorporated by reference.

Operating conditions for the dehydrogenation reaction zone are specifically selected to provide low conversion. Operating conditions for the preferred dehydrogenation zone of this invention will usually include an operating temperature in the range of from 950° to 1200° F., with an operating temperature of at least 1100° F. being preferred and with an operating temperature of about 1130° F. being particularly preferred. A relatively high operating pressure characterizes the low conversion conditions of the preferred dehydrogenation zone and is usually within a range of 30 to 150 psig. Pressures for the preferred dehydrogenation zone are more typically at least 50 psig, with pressures of about 70 to 110 psig being particularly preferred. Low conversion conditions will also permit the operation of the dehydrogenation zone at low hydrogen to hydrocarbon ratios in a range of from 0.1 to 4 and more preferably about 0.2. Space velocities for the dehydrogenation zone range from 0.5 to 50 and will normally exceed 10 and will typically equal about 15. Further extension of the catalyst life from the typical 4 to 6 days may be obtained by operating with lower space velocities.

Most typical multireactor arrangements for the dehydrogenation zone will have interstage heating between reactors that establish adiabatic conditions through the reactors. Further improvements in catalyst life and reactor stability may be obtained by operating the reactor isothermally or with an ascending temperature profile over the reactant path of the reactor. Isothermal conditions or ascending temperature profiles may be established by indirect heat exchange between the reactants or catalyst beds within the reaction zone and a circulating heat exchange medium. Such reactor arrangements can include internal heating means within the catalyst bed. Useful arrangements for internal heating of reactants can employ tubes or channels for indirect heating with catalyst and reactants on one side of a heat exchange surface and a heating medium on the opposite side. Other heating arrangements for the reactor bed may integrate a fired heater wherein catalyst is contained within tubes that occupy the combustion chamber of heater.

Low conversion and lower temperatures for the dehydrogenation reaction zone also promote savings in equipment. Higher pressures within the dehydrogenation zone and its integration with the saturation reaction zone also reduces the equipment expense associated with hydrogen supply and recovery. The relatively high pressures within the dehydrogenation zone can result in the recovery of a hydrogen stream having purities of 40% or greater with minimal cooling. The low conversion operation of the dehydrogenation zone allows utilization of such a low purity hydrogen stream due to the high amount of isobutane recycle that dilutes the harmful effect of any olefin carryover to the dehydrogenation zone. In addition, the supply of the excess hydrogen from the dehydrogenation zone to the saturation zone results in the recovery of excess $IC_4$ material in the primary fractionator which would otherwise pose an unacceptable loss of these hydrocarbons in the operation of the process.

The effluent from the dehydrogenation will normally undergo recovery of hydrogen and removal of aromatics that are produced as the by-products from the preferred dehydrogenation process. Apart from heat exchange and pressurization all remaining portions of the dehydrogenation zone effluent will typically pass directly to the oligomerization zone.

The addition of an olefin feed downstream of the dehydrogenation zone separator can be beneficial to the efficient and advantageous performance of this process. The source of the olefin input stream is typically a light gas stream recovered from the gas separation section of an FCC process. Other sources for suitable olefin feeds will also include $C_4$ streams from steam cracking and coker off gas. The olefin feed stream is characterized by having an overall $C_4$ olefin concentration of at least 10 wt %. In most operations, this olefin feed stream will contain $C_4$ olefins, but it may also constitute all or substantial quantities of $C_3$ olefins. Typically the olefin feeds can have a $C_3$ to $C_5$ olefin concentration of at least 30 wt %. Preferred olefin feeds will have a $C_4$ olefin concentration of at least 30 wt % and more preferably at least 50 wt %. Preferably the olefin feed stream will comprise at least 20 wt % and more preferably 30 wt % isobutene. The isobutene will preferably comprise at least 33% of the total butenes. The olefin content of preferred feeds will predominately comprise branched olefins with isobutene present in large quantities. The reaction of normal pentenes and propylene is promoted by maintaining a high concentration of isobutene in the feed to the oligomerization zone of this invention. Oligomerization of pentene and propylene into high octane isomers is promoted by having an olefin distribution in the feed to the isomerization zone that comprises at least 50 wt % isobutene. When large quantities of propylene are present in the feed to the oligomerization zone, the octane number of the product may be increased by raising the percentage of isobutene in the butene fraction of the feed. Preferably the butene fraction will comprise 65% isobutene when large amounts of propylene enter the oligomerization zone.

Suitable oligomerization zones for this invention take on many forms. The oligomerization process is known by many names such as catalytic condensation and also as catalytic polymerization. Known catalysts for effecting such reactions include heterogeneous catalysts such as Y zeolites, beta zeolites, silicalite, and sulfonated resins as well as homogenous catalysts such as borontrifluoride as described in U.S. Pat. Nos. 3,906,053, 3,916,019 and 3,981,941.

The preferred catalyst for the oligomerization process is a solid phosphoric acid (SPA) catalyst. As previously mentioned, the SPA catalyst refers to a solid catalyst that contains as a principal ingredient an acid of phosphorous such as ortho -pyro- or tetraphosphoric acid. The catalyst is normally formed by mixing the acid of phosphorous with a siliceous solid carrier to form a wet paste. This paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth, and diatomaceous earth. A minor amount of various additives such as mineral talc, fuller's earth, and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this such as a lower phosphoric acid content are, however, possible. Further details as to the composition and production of SPA catalysts may be obtained from U.S. Pat. Nos. 3,050,472; 3,050,473, and 3,132,109 and from other references.

Oligomerization zones in general are maintained at conditions which may vary widely due to the previously listed variables. In this invention the oligomerization reaction zone is operated at temperatures and pressures that increase compatibility with the dehydrogenation reaction zone effluent and the feed of the oligomerization reaction zone to the saturation reaction zone. A broad range of suitable pressures is from about 15 psig to about 1200 psig. The recycle of $C_8$ and heavier paraffins from the saturation zone has been found in some cases to improve the selectivity of the oligomerization reaction zone to $C_8$ olefin production.

In the preferred embodiment, an SPA catalyst is utilized in a chamber-type reactor to form an effluent containing $C_5$ through $C_{12}$ hydrocarbons having boiling points within a gasoline boiling point range of about 100° F. to about 450° F. as determined by the appropriate ASTM distillation method. The preferred temperature of the oligomerization reaction zone will typically be in a range of from 200° to 500° F. and will more typically be in a range of from 300° to 450° F. Pressures within the oligomerization reaction zone will usually be in a range of from 200 to 1200 psig and will more typically be in a range of from 200 to 600 psig. Steam or water may be fed into the reactor to maintain the desired water content in the preferred catalyst.

The catalyst is preferably disposed in fixed beds within the oligomerization zone in what is known as a chamber-type reactor structure. In a chamber-type reactor, the reactants flow through a series of large diameter catalyst beds. The temperature of the reactants is controlled by recycling relatively inert hydrocarbons which act as a heat sink. The unreacted isobutane from the dehydrogenation zone supplies a large proportion of the inert hydrocarbons that act as the heat sink. Temperature control within the oligomerization reaction zone is also promoted by the use of a quench material. A quench material that comprises the inert materials and heavy product material from the saturation zone may be used simultaneously for temperature control. The quench material serves as its primary advantage of the control of temperatures within the oligomerization reaction zone. As a secondary purpose, the quench material can provide a flushing function to inhibit the development of coke and the deactivation of coke in the deactivation of the catalyst within the reaction zones. As pressure within the oligomerization reaction zone decreases, the flushing function of the quench material decreases as the vaporization of the reactants and quench within the reaction zone increase. The use of higher molecular weight quench material within the oligomerization reaction zones to inhibit coking while permitting lower pressure operation is one possible method for the operation of this invention. Thus, the addition of heavier quench materials facilitates the operation of the oligomerization zone at higher temperatures and lower pressures while still flushing the catalyst and preventing coke production. The recycle of higher molecular weight paraffins, such as $C_8$ and heavier hydrocarbons from the saturation effluent, can also improve selectivity of the oligomerization zone to produce the desired $C_7+$ olefin products. Since the higher molecular weight materials have benefits beyond use as a quench, it can be beneficial to add all of or a portion of such material to the inlet of oligomerization reactor with the feed.

The different catalyst beds are preferably contained within one or more cylindrical, vertically oriented vessels and the feed stream preferably enters the top of the reactor. Typically, a chamber-type reactor will contain about five catalyst beds.

With the addition of the olefin input stream the combined feed to the oligomerization zone will preferably have a ratio of paraffins to olefins of from 1:1 to 5:1. Typically the paraffin concentration of the feed to the oligomerization reaction zone will be at least 50 wt % and more typically will be at least 70 wt %. A high percentage of the olefins in the feed stream entering the process as the secondary feed stream upstream are reacted in the oligomerization reaction zone along with the isobutene with olefin conversions in the range of from 80 to 99%. The principal oligomerization products comprise $C_7+$ olefins.

The oligomerization effluent containing principally isobutane and the olefinic gasoline components passes to the saturation reactor. Suitable saturation reactors will provide an essentially complete saturation of all olefins from saturation reactor. The effluent from the oligomerization zone will preferably pass directly to the saturation zone without separation or recovery of light ends. Lower pressure operation for the oligomerization reactor is preferred to allow direct passage of the polymerization effluent to the hydrogenation reactor. The saturation zone will typically operate at higher temperatures than the oligomerization zone so that quench fluid and paraffins in the effluent from the oligomerization will provide additional heat sink material for the higher operating temperatures of the saturation reaction zone.

Before entering the saturation zone the oligomerization effluent is first mixed with a hydrogen-containing gas stream. The gas stream should contain at least 50 wt % of hydrogen. Preferably, the hydrogen-containing gas stream will have a hydrogen concentration greater than 75 wt % hydrogen. Hydrogen recovered from the dehydrogenation section supplies a major amount of the hydrogen input for the saturation zone with the remainder of the necessary hydrogen supplied from outside sources as a make-up hydrogen. High purity is preferred for the make-up hydrogen to increase the overall purity of the hydrogen entering the saturation zone thereby reducing the volume of light hydrocarbons. These light hydrocarbons are undesirable since their presence needlessly increases the mass volume through the saturation reaction zone and their relatively high vapor pressure can increase the loss of isobutane in the deisobutanizer column.

The make-up gas stream is mixed with the oligomerization effluent in proportions that will produce a hydrogen to hydrocarbon ratio in a range of 0.1 to 2. and more preferably in a range of from 0.15 to 0.30. Preferably the saturation zone of this invention will comprise a hydrotreater section that requires a hydrogen to hydrocarbon ratio of not more than 0.9 stdm$^3$/m$^3$ (50 SCFB) at the effluent of the saturation reactor.

The preferred saturation reactor of this invention will provide an essentially complete saturation of all unsaturated hydrocarbons. Conditions within the hydrotreating zone typically include a temperature in the range of 200°–600° F., a pressure of from 100 to 1000 psig, and a liquid hourly space velocity of from 1 to 20. Preferably, the reaction conditions are selected to keep the hydrocarbon feed in a vapor phase. The hydrotreater arrangement will generally operate at temperatures that permit the raising of the combined feed stream to reaction temperatures by heat exchange with hydrotreater effluent. In this manner any heat importation into the oligomerization and hydrogenation sequence can preferably be made by a trim heater on the inlet stream to the oligomerization reaction zone.

The preferred hydrotreatment reactor contains a fixed bed of hydrotreatment catalyst. Catalytic composites that can be used in this process include traditional hydrotreating catalysts. Combinations of clay and alumina-containing metallic elements from Group VIII alone and from both Group VIII and Group VIB of the Periodic Table have been found to be particularly useful. Group VIII elements include iron, cobalt, nickel, ruthenium, rhenium, palladium, osmium, indium and platinum with cobalt and nickel being particularly preferred. The Group VIB metals consist of chromium, molybdenum and tungsten, with molybdenum and tungsten being particularly preferred. The metallic components are supported on a porous carrier material. The carrier material may comprise alumina, clay or silica. Particularly useful catalysts are those containing a combination of cobalt or nickel metals ranging from 2.0 to 5 wt % and from 5 to 15 wt % molybdenum on an alumina support. The weight percentages of the metals are calculated as though they existed in the metallic state. Typical commercial catalysts comprise spherical or extruded alumina based composites impregnated with Co—Mo or Ni—Mo in the proportions suggested above. Other useful catalyst compositions 15 to 20 wt. % nickel on alumina. The ABD of commercial catalysts generally range from 0.5 to 0.9 g/cc with surface areas ranging from 150 to 250 m$^2$/g. Generally, the higher the metals content on the catalyst, the more active the catalyst.

Effluent from the saturation reaction zone enters a quench separator. The quench separator divides a high proportion of the C$_4$ and lower boiling materials from the saturation zone effluent to provide a quench stream with a relatively higher concentration of C$_7$ and heavier hydrocarbons. The recovery of the higher molecular weight material from the effluent of the saturation reaction zone benefits the integration of the oligomerization reaction zone and the saturation reaction zone. The recycle of the C$_7$ and heavier hydrocarbons provides a nonreactive stream that permits a liquid concentration to be maintained in the oligomerization reaction zone at lower pressures. Lowering of the pressure in the oligomerization reaction zone reduces the cost or compression between typical saturation reaction zones and the dehydrogenation zone while providing the necessary wash to keep the oligomerization zone catalyst clean. Except for any volume that recirculates as quench, all of the remaining effluent from the saturation reaction zone will preferably enter the primary separation column to complete the flow scheme of the invention as described.

EXAMPLE

To more fully demonstrate the attendant advantages of the present invention, the following example is based on thermodynamic analysis and engineering calculations. The example presents the operation of the invention using a separation section, a dehydrogenation section, a single compressor, an oligomerization section, and a hydrogenation section. As with the FIGURE, details such as miscellaneous pumps, heaters, coolers, valving, start-up lines and similar hardware have been omitted as being non-essential to a clear understanding of the techniques involved.

Feed input streams containing 41.5 mol % isobutane and 57.9 mol % normal butane enters the process at a mass rate of 4700 lb-mol/hr. Other lesser components of the feed input streams include 0.2 mol % butene and 0.4 mol % pentane. The feed input stream enters a deisobutanizer column in the separation section that also receives a recycle stream comprising 60 lb mol/hr propane, 1075 lb mol/hr isobutane and 65 lb mol/hr butane. The recycle stream enters the deisobutanizer column at a temperature of 152° F. and a pressure of 150 psi. The isobutane feed stream for the dehydrogenation zone is recovered from the deisobutanizer column and combined with an additional portion of the recycle stream to provide a feedstream having the composition given in the table for stream A. 1425 lb mol/hr hydrogen for the dehydrogenation zone having a hydrogen purity of 78 mol % with the remainder of the gas stream comprising mainly 4.6 mol % methane, 2.1 mol % C$_3$'s, 10 mol % isobutane, and 4.1 mol % isobutene is combined with the feed input stream and heated to produce a combined feed input stream. The combined feed stream enters the dehydrogenation zone at a temperature of about 1171° F. and a pressure of 75 psi. The feed stream passes through two stages of dehydrogenation where it contacts a dehydrogenation zone catalyst comprising 0.6 wt % platinum, 0.3 wt % tin, 0.70 wt % potassium and 0.1 wt % Cl on a theta alumina base. After heat exchange with the incoming feed, the dehydrogenation zone effluent is further cooled to a temperature of about 100° F. before entering a single casing compressor. The compressor discharges an effluent at a pressure of about 570 psig into a separator that recovers an overhead stream that supplies hydrogen to the dehydrogenation zone and a saturation zone.

| | Stream | | | | |
|---|---|---|---|---|---|
| Mole % | A | B | C | D | E |
| H$_2$ | — | 2.7 | 16.3 | 6.8 | |
| C$_1$ | — | .8 | 1.5 | 1.4 | |
| C$_2$ | — | .2 | .2 | .2 | |
| C$_3$ | 3.6 | 3.8 | 3.9 | 4.5 | |
| C$_3$= | | .6 | .1 | | |
| IC$_4$ | 91.5 | 52.6 | 54.2 | 65.4 | .9 |
| IC$_4$= | | 20.2 | 1.8 | | |
| NC$_4$ | 4.9 | 3.2 | 3.3 | 40.7 | .8 |
| 1-NC$_4$= | | .2 | .1 | | |
| C2—NC$_4$= | | .2 | .1 | | |
| T2—NC$_4$= | | .3 | .1 | | |
| C$_6$ | — | — | — | | .1 |
| C$_7$= | | | .3 | | |
| C$_7$ | .2 | .2 | | .4 | 3.9 |
| C$_8$= | | | 5.7 | | |
| C$_8$ | 5.2 | 3.9 | | 9.2 | 78.4 |
| C$_9$= | | | — | | |
| C$_9$ | .1 | — | | .1 | .4 |
| C$_{12}$= | | 1.0 | | | |
| C$_{12}$ | 9.3 | 7.1 | | 7.7 | 14.3 |
| PX | .2 | .1 | | .1 | .9 |
| TOL | | | | | .2 |

The bottoms stream from the separator provides a feed to the oligomerization zone. The separator bottoms stream is combined with a heavy recycle stream to provide 62,400 lbs/hr of a feed to the oligomerization zone having the composition given in the table for stream B. The oligomerization zone contains an SPA catalyst that contacts the feed fractions at a temperature of about 310° F. and a pressure of about 545 psi. Temperature rise in the oligomerization reaction zone is controlled by the presence of unreacted isobutane as well as the addition of the quench medium at intermediate locations along the reactors.

Recovered hydrogen combined with the oligomerization zone effluent provide a feed to the saturation zone having the composition given in the table for stream C. The feed enters the hydrogenation reactors at a temperature of about 450° F. and a pressure of about 528 psig. The saturation zone has two hydrotreating reactors that contact the feed with a saturation catalyst comprising 15–20 wt-% nickel on an aluminum base. About 1450 lb mol/hr of an isobutane is intermixed with the intermediate effluent between the hydrotreating reaction zones. The effluent from the saturation zone has the composition given for stream D.

After heat exchange and recovery of quench materials, the remaining effluent from the hydrotreating reactors passes to a separation section at a temperature of 300° F. and a pressure of 250 psi and under goes further separation to remove light ends and recover $C_4$ hydrocarbons. An off gas stream comprising 820 lb mol/hr of hydrogen and 310 lb mol/hr of $C_3$ and lighter hydrocarbon gases are recovered from the further separation of the saturation zone effluent.

The remaining portion of the saturation zone effluent undergoes further separation. A debutanizer recovers a net bottoms stream as a product having the composition given for stream E. The overhead from the debutanizer comprises 5.0 mol % propane, 89.6 mol % isobutane and 5.4 mol % normal butane. About 40% of the debutanizer overhead is recycled to the oligomerization section as quench and about 15% of the debutanizer is passed to the deisobutanizer for further separation of normal butanes and recycle to the dehydrogenation zone. The remaining 45% of the debutanizer overhead passes directly to the dehydrogenation zone. A net sidecut of stream comprising about 2480 lb mol/hr of normal butane is also recovered from the deisobutanizer.

As the example demonstrates, the highly efficient arrangement of this process produces an alkylate quality gasoline with a highly efficient integration that uses only one compressor section.

What is claimed is:

1. A process for the production of a motor fuel product from an isobutane-containing input stream, said process comprising:
   a) passing at least a portion of said input stream comprising isobutane to a dehydrogenation zone and contacting C4 hydrocarbons in said dehydrogenation zone with a dehydrogenation catalyst at dehydrogenation conditions including a temperature of 950° to 1200° F. and a pressure of from 5 to 150 psig and an LHSV of 0.5–50 and recovering hydrogen and a dehydrogenation effluent comprising C4 isoolefins and isobutane;
   b) passing at least a portion of said dehydrogenation zone effluent to a compressor and compressing said effluent to a pressure of at least 450 psig to produce a compressed effluent;
   c) passing said compressed effluent to a first separator and recovering from said separator a first separator stream comprising hydrogen at a pressure of from 400 to 600 psig and a dehydrogenated fraction comprising $C_4$ olefins and paraffins in a liquid phase;
   d) passing at least a portion of said dehydrogenated fraction to an oligomerization zone as an oligomerization feed and contacting said oligomerization zone feed with a solid oligomerization catalyst at oligomerization conditions including a temperature of 200° to 500° F., a pressure of 400 to 600 psig, and an LHSV of 0.8 to 5 to recover an oligomerization effluent comprising C7 and higher isoolefins;
   e) passing at least a portion of the effluent from the oligomerization zone into a saturation zone and passing at least a portion of said first separator stream into said saturation zone and contacting said oligomerization zone effluent and hydrogen with a saturation catalyst at saturation conditions to saturate olefins in said oligomerization effluent and recovering a saturation zone effluent stream;
   f) passing at least a portion of said saturation zone effluent stream to a second separator and recovering from said second separator a second separator stream comprising $C_7$ or higher hydrocarbons in liquid phase and a third separator stream comprising $C_4$ and lower boiling hydrocarbon vapors;
   g) passing a first portion of said second separator stream to said oligomerization zone as a recycle stream; and,
   h) recovering said motor fuel product from a second portion of said second separator stream.

2. The process of claim 1 wherein the saturation zone comprises a hydrotreater.

3. The process of claim 1 wherein the olefin concentration of the oligomerization zone feed stream is at least 50 wt % isobutene.

4. The process of claim 1 wherein a first feed stream comprising isobutane is charged to a deisobutanizer and said first input stream is recovered from said deisobutanizer as a sidecut stream.

5. The process of claim 1 wherein said dehydrogenation zone catalyst comprises platinum, tin and potassium metals on an alumina base.

6. The process of claim 5 wherein said dehydrogenation zone catalyst further comprises theta alumina.

7. The process of claim 1 wherein said dehydrogenation zone operates at a pressure of less than 110 psig.

8. The process of claim 1 wherein said dehydrogenation zone effluent contains less than 35 wt % olefins, and a hydrogen feed is combined with said dehydrogenation zone effluent that enters said compressor.

9. The process of claim 1 wherein a second input stream comprising $C_4$ olefins is charged to said oligomerization zone.

10. The process of claim 1 wherein said recycle stream comprises a quench stream.

11. The process of claim 1 wherein said recycle stream is charged to the inlet of the reactors in said oligomerization zone.

12. The process of claim 1 wherein said portion of said first separator stream passes directly into said saturation zone.

13. A process of claim 1 wherein at least a portion of said third separator stream is recycled to said dehydrogenation zone.

14. The process of claim 13 wherein said third separator stream is passed to a debutanizer and a portion of the debutanizer overhead stream is recycled directly to said dehydrogenation zone.

15. A process for the production of motor fuel product components from an isobutane- containing feed stream, said process comprising:

a) passing said isobutane feed stream and a recycle stream comprising $C_4$ hydrocarbons and motor fuel products to a deisobutanizer column;

b) recovering a dehydrogenation feed comprising at least 80 wt % isobutane from said deisobutanizer column;

c) combining said dehydrogenation zone feed with a hydrogen stream to produce a combined dehydrogenation zone feed having a hydrogen to hydrocarbon ratio of 0.1 to 4;

d) passing said combined dehydrogenation feed to a dehydrogenation zone and contacting the dehydrogenation zone feed with a dehydrogenation catalyst comprising a platinum, tin and potassium metals on an alumina base at dehydrogenation conditions including a temperature of 1100° to 1200° F., a pressure of 5 to 150 psig and a LHSV of 10 to 50, and recovering a dehydrogenation effluent comprising isobutene and hydrogen;

e) compressing said dehydrogenation zone effluent stream to a pressure of from 450 to 600 psig in a compressor to produce a compressed effluent;

f) passing at least a portion of said compressed effluent to a first separator and recovering from said first separator a hydrogen stream having a purity of at least 80 mol % and a dehydrogenated fraction comprising $C_4$ olefins and paraffins in a liquid phase;

g) passing said dehydrogenated fraction to an oligomerization zone without further compression, contacting said oligomerization zone feed with multiple beds of a solid phosphoric acid catalyst at oligomerization conditions including a temperature of 200° to 500° F., a pressure of 400 to 600 psig, and an LHSV of 1 to 4, and injecting a first quench stream comprising $C_7$ and higher paraffins into said multiple beds to produce an oligomerization effluent comprising $C_8$ isoolefins;

h) passing a portion of said hydrogen stream to a hydrotreating reaction zone without further compression and passing said oligomerization zone effluent stream without separation into a hydrotreating reaction zone comprising multiple beds of a solid hydrotreating catalyst to saturate olefins and obtain an essentially complete saturation of said $C_8$ isoolefins, injecting a second quench stream between beds of said hydrotreating catalyst and recovering a hydrotreated effluent stream;

i) passing at least a portion of said hydrotreated effluent stream to a second separator to separate a heavy hydrocarbon stream comprising $C_7$ or higher hydrocarbons and supplying said first and second quench streams from a first portion of said heavy hydrocarbon stream;

j) passing a second portion of said heavy hydrocarbon stream to said deisobutanizer column as said recycle stream; and k) recovering a bottoms stream comprising said motor fuel product components from said deisobutanizer.

16. The process of claim 15 wherein said first compressed stream passes from said compressor to a third separator, and a bottoms stream comprising $C_8$ and heavier hydrocarbons is recovered in said third separator and the remainder of said compressed stream passes to said first separator.

17. The process of claim 15 wherein the oligomerization temperature of said oligomerization zone is in a range of from 300° to 320° F.

* * * * *